(12) United States Patent
Faruqi

(10) Patent No.: US 6,368,801 B1
(45) Date of Patent: Apr. 9, 2002

(54) DETECTION AND AMPLIFICATION OF RNA USING TARGET-MEDIATED LIGATION OF DNA BY RNA LIGASE

(75) Inventor: A. Fawad Faruqi, Guilford, CT (US)

(73) Assignee: Molecular Staging, Inc.

( * ) Notice: Subject to any disclaimer, the term of this patent is extended or adjusted under 35 U.S.C. 154(b) by 0 days.

(21) Appl. No.: 09/547,757

(22) Filed: Apr. 12, 2000

(51) Int. Cl.⁷ .............................. C12Q 1/68; C12P 19/34
(52) U.S. Cl. ........................ 435/6; 435/91.1; 435/91.2
(58) Field of Search .......................... 435/6, 91.1, 91.2

(56) References Cited

U.S. PATENT DOCUMENTS

| | | | |
|---|---|---|---|
| 5,187,060 A | 2/1993 | Cerruti et al. | 435/5 |
| 5,429,807 A | 7/1995 | Matson et al. | 422/131 |
| 5,516,663 A | 5/1996 | Backman | 435/91.2 |
| 5,599,695 A | 2/1997 | Pease et al. | 435/91.1 |
| 5,654,413 A | 8/1997 | Brenner | 536/22.1 |
| 5,770,408 A | 6/1998 | Sato | 435/91.2 |
| 5,800,994 A | 9/1998 | Martinelli et al. | 435/6 |
| 5,807,674 A | 9/1998 | Tyagi | 435/6 |
| 5,854,033 A | 12/1998 | Lizardi | 435/91.2 |
| 5,871,914 A | 2/1999 | Nathan | 435/6 |
| 5,871,928 A | 2/1999 | Fodor et al. | 435/6 |
| 5,876,924 A * | 3/1999 | Zhang et al. | 435/5 |
| 5,888,731 A | 3/1999 | Yager et al. | 435/6 |
| 5,912,148 A | 6/1999 | Eggerding | 536/91.2 |
| 5,942,609 A | 8/1999 | Hunkapiller et al. | 536/25.3 |
| 5,959,095 A | 9/1999 | Martinelli et al. | 536/24.32 |
| 5,962,223 A | 10/1999 | Whiteley et al. | 435/6 |
| 5,998,175 A | 12/1999 | Akhaven-Tafti | 435/91.5 |
| 6,020,138 A | 2/2000 | Akhaven-Tafti | 435/6 |
| 6,025,139 A | 2/2000 | Yager et al. | 435/6 |
| 6,027,889 A | 2/2000 | Barany et al. | 435/6 |

FOREIGN PATENT DOCUMENTS

| | | |
|---|---|---|
| EP | 0 320 308 A2 | 12/1988 |
| WO | WO 95/22623 A1 | 8/1995 |
| WO | WO 97/20948 A1 | 6/1997 |

OTHER PUBLICATIONS

Kinoshita, Y. et al., "Strand Ligation in Double–stranded DNA by T4 RNA Ligase", Chemistry Letters, p. 797–798 (1996).*

Baner, et al., "Signal amplification of padlock probes by rolling circle replication," *Nucleic Acids Res.* 26(22):5073–8 (1998).

(List continued on next page.)

Primary Examiner—Kenneth R. Horlick
Assistant Examiner—Teresa Strzelecka
(74) Attorney, Agent, or Firm—Needle & Rosenberg, P.C.

(57) ABSTRACT

Disclosed are techniques for detection of nucleic acids, amplification of nucleic acids, or both, involving ligation by T4 RNA ligase of DNA strands hybridized to an RNA strand. These techniques are particularly useful for the detection of RNA sequences and for amplification of nucleic acids from, or dependent on, RNA sequences. It has been discovered that T4 RNA ligase can efficiently ligate DNA ends of nucleic acid strands hybridized to an RNA strand. In particular, this ligation is more efficient than the same ligation carried out with T4 DNA ligase. Thus, techniques involving ligation of DNA ends of nucleic acid strands hybridized to RNA can be performed more efficiently by using T4 RNA ligase. Many known ligation-based detection and amplification techniques are improved through the use of T4 RNA ligase acting on DNA strands or ends. Such techniques include ligase chain reaction (LCR), ligation combined with reverse transcription polymerase chain reaction (RT PCR), ligation-mediated polymerase chain reaction (LMPCR), polymerase chain reaction/ligation detection reaction (PCR/LDR), ligation-dependent polymerase chain reaction (LD-PCR), oligonucleotide ligation assay (OLA), ligation-during-amplification (LDA), ligation of padlock probes, open circle probes, and other circularizable probes, and iterative gap ligation (IGL).

36 Claims, 4 Drawing Sheets

OTHER PUBLICATIONS

Becker & Maher, "LMPCR for detection of oligonucleotide- directed triple helix formation: a cautionary note," *Antisense Nucleic Acid Drug Dev.* 9(3):313–6 (1999).

Brennan, et al., "Using T4 RNA ligase with DNA substrates," *Methods in Enzymology* 100(Part B):38–52 (1983).

Brian Johnston, (IBCs Fifth Annual International Conference on "Antisense: DNA and RNA Based Therapeutics," Feb. 2–3, 1998, Coronado, CA).

Chen & Ruffner, "Amplification of closed circular DNA in vitro," *Nucleic Acids Res.* 26(23):1126–7 (1998).

Gasparini, et al., "Analysis of 31 CFTR mutations by polymerase chain reaction/oligonucleotide ligation assay in a pilot screening of 4476 newborns for cystic fibrosis," *J. Med. Screen.* 6(2):67–9 (1999).

Guo, et al., "Direct fluorescence analysis of genetic polymorphisms by hybridization with oligonucleotide arrays on glass supports," *Nucleic Acids Res.* 22(24):5456–5465 (1994).

Hermanson, et al., eds., *Immobilized Affinity Ligands*, (Academic Press, New York, 1992).

Hinton, et al., "The preparative synthesis of oligodeoxyribonucleotides using RNA ligase," *Nucleic Acids Res.* 10(6):1877–94 (1982).

Hoy, et al., "Bromodeoxyuridine/DNA analysis of replication in CHO cells after exposure to UV light," *Mutation Research* 290:217–230 (1993).

Hsuih, et al., "Novel, ligation–dependent PCR assay for detection of hepatitis C in serum," *J. Clin. Microbiol.* 34(3):501–7 (1996).

Hsuih, et al., "Quantitative Detection of HCV RNA Using Novel Ligation–Dependent Polymerase Chain Reaction", *American Association for the Study of Liver Diseases*, (Chicago, IL, Nov. 3–7, 1995) [poster abstract].

Johnstone & Thorpe, *Immunochisry In Practice* (Blackwell Scientific Publications, Oxford, England, 1987) pp. 209–216 and 241–242.

Kerkhof, "A Comparison of Substrates for Quantifying the Signal from a Nonradiolabeled DNA Probe," *Analytical Biochemistry* 205:359–364 (1992).

Khrapko, et al., "Hybridization of DNA with Oligonucleotides Immobilized in Gel: A Convenient Method for Detecting Single Base Substitutions," *Molecular Biology (Mosk) (USSR)*25:718–730 (1991).

Laffler, et al., "The ligase chain reaction in DNA–based diagnosis," *Ann. Biol. Clin. (Paris)*.51(9):821–6 (1993).

Langer, et al., "Enzymatic synthesis of biotin–labeled polynucleotides: Novel nucleic acid and affinity probes", *Proc. Natl. Acad. Sci. USA* 78(11):6633–6637 (1981).

Lee, "Ligase chain reaction," *Biologicals* 24(3):197–9 (1996).

Mccoy & Gumport, "T4 Ribonucleic acid ligase joins single-strand oligo(deoxyribonucletides), "*Biochemistry* 19(4):635–42 (1980).

Moore & Sharpe, "Site–specific modification of pre–mRNA: the 2'–hydroxyl groups at the splice sites,"*Science* 256(5059):992–7 (1992).

Nilsson, et al., "Padlock Probes: Circularizing Oligonucleotides for Localized DNA Detection," *Science* 265:2085–2088 (1994).

Park, et al., "Detection of hepatitis C virus RNA using ligation–dependent polymerase chain reaction in formalin––fixed, paraffin–embedded liver tissues," *Am. J. Pathol.* 149(5):1485–91 (1996).

Pease, et al., "Light–generated oligonucleotide arrays for rapid DNA sequence analysis," *Proc. Natl. Acad. Sci. USA* 91(11):5022–5026 (1994).

Rodriguez & Akman, "Large scale isolation of genes as DNA fragment lengths by continuous elution electrophoresis through an agarose matrix," *Electrophoresis* 19(5):646–52 (1998).

Schena, et al., "Quantitative Monitoring of Gene Expression Patterns with a Complementary DNA Microarray," *Science* 270:467–470 (1995).

Silber, et al., Purification and properties of bacteriophage T4–induced RNA ligase, *Proc. Natl. Acad. Sci. U. S. A.* 69(10):3009–13 (1972).

Stefano, et al., "Rapid and sensitive detection of Chlamydia trachomatis using a ligatable binary RNA probe and Q beta replicase," *Mol. Cell. Probes* 11(6):407–26 (1997).

Stewart, et al., "A quantitative assay for assessing allelic proportions by iterative gap ligation," *Nucleic Acids Res.* 26(4):961–6 (1998).

Stimpson, et al., "Real–time detection of DNA hybridization and melting on oligonucleotide arrays by using optical wave guides," *Proc. Natl. Acad. Sci. USA* 92(14):6379–6383 (1995).

Syvänen, et al., "Fast quantification of nucleic acid hybrids by affinity–based hybrid collection," *Nucleic Acids Res.* 14(12):5037–48 (1986).

Taylor, ed, *Protein immobilization: fundamentals and applications* (M. Dekker, New York, 1991).

Tessier, et al., "Ligation of single–stranded oligodeoxyribonucleotides by T4 RNA ligase," *Analytical Biochem.* 158:171–178 (1986).

Thomas, et al., "Amplification of padlock probes for DNA diagnostics by cascade rolling circle amplification or the polymerase chain reaction," *Arch. Pathol. Lab. Med.* 123(12):1170–6 (1999).

Tobe, et al., "Single–well genotyping of diallelic sequence variations by a two–color Elisa–based oligonucleotide ligation assay," *Nucleic Acids Res.* 24(19):3728–32 (1996).

Wansink, et al., "Fluorescent Labeling of Nascent RNA Reveals Transcription by RNA Polymerase II in Domains Scattered Throughout the Nucleus," *Journal of Cell Biology* 122(2): 283–293 (1993).

Wiedmann, et al., "Ligase Chain Reaction (LCR)—Overview and Applications," *PCR Methods and Applications* (Cold Spring Harbor Laboratory Press, Cold Spring Harbor Laboratory, NY, 1994) pp. S51–S64.

Yu, et al. "Cyanine dye dUTP analogs for enzymatic labeling of DNA probes," *Nucleic Acids Research* 22(15): 3226–3232 (1994).

Zhang, et al., "Amplification of target–specific, ligation–dependent circular probe," *Gene* 211(2):277–85 (1998).

Zirvi, et al., "Ligase–based detection of mononucleotide repeat sequences," *Nucleic Acids Res.* 27(24):e40 (1999).

* cited by examiner

Elimination of the non-specific signal from mismatch ligation

• Real-Time ERCA of ligation done in the presence of 10% formamide

SEQUENCE LISTING

<160> NUMBER OF SEQ ID NOS: 1

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      Target

<400> SEQUENCE: 1
gaaaggcctt gtggtactgc ctgatagggt gcttgcgagt gccccgg                    47

DETECTION AND AMPLIFICATION OF RNA USING TARGET-MEDIATED LIGATION OF DNA BY RNA LIGASE

BACKGROUND OF THE INVENTION

The disclosed invention is generally in the field of detection and amplification of nucleic acids, and in particular involves detection and amplification based on target-specific ligation of oligonucleotides.

Numerous techniques for detection and/or amplification of nucleic acids are known. A number of these involve ligation of oligonucleotides. Such techniques include ligase chain reaction (LCR; Wiedmann et al., PCR Methods Appl. 3(4):S51–64 (1994); U.S. Pat. No. 5,516,663 to Backman et al.), ligation-mediated polymerase chain reaction (LMPCR; Rodriguez and Akman, Electrophoresis 19:646–652 (1998)), ligation-dependent polymerase chain reaction (LD-PCR; Park et al., Am J Pathol 149(5):1485–1491 (1996)), oligonucleotide ligation assay (OLA; Tobe et al., Nucleic Acids Res. 24:3728–3732 (1996)), and ligation of padlock probes or open circle probes (Nilsson et al., Science 265:2085–2088 (1994); U.S. Patent No. 5, 854,033 to Lizardi).

These techniques generally involve ligation of DNA ends by T4 DNA ligase or other DNA ligases. Many ligation-based techniques involve ligation of the oligonucleotides hybridized to another nucleic acid strand and generally depend on the ends of the oligonucleotides being adjacent to each other. Some DNA ligases can ligate the ends of DNA strands hybridized to an RNA strand. T4 DNA ligase is an example of this (Hsuih et al., Quantitative detection of HCV RNA using novel ligation-dependent polymerase chain reaction, American Association for the Study of Liver Diseases, Abstract 1002 (Chicago, Ill., Nov. 3–7, 1995)).

T4 RNA ligase joins a 3'-hydroxyl-terminated acceptor oligoribonucleotide to a 5'-phosphate-terminated donor oligoribonucleotide. (Silber et al., Proc. Natl. Acad. Sci. USA 69:3009 (1972)). As its name denotes, T4 RNA ligase is principally know for ligation of RNA ends. Studies with T4 RNA ligase revealed that it could catalyze the formation of a phosphodiester bond between the 3' hydroxyl and 5' phosphate of short oligonucleotides (Brennan et al., Methods in Enzymology 100(Part B):38–52 (1983); Tessier et al., Analytical Biochem. 158:171–178 (1986)). The reactions required high concentrations of nucleic acids and were not efficient. These studies did not attempt ligation of DNA strands when hybridized to RNA. RNA-directed RNA ligase has been used to ligate RNA probes hybridized to a target sequence (U.S. Pat. No. 5,807,674). This ligation was used to detect specific sequences to which pairs of RNA probes would hybridize. T4 DNA ligase was the preferred ligase.

RNA molecules hybridized to RNA or DNA strands have been ligated. For example, ligation of RNA padlock probes hybridized to mRNA was described by Brian Johnston (IBCs Fifth Annual International Conference on "Antisense: DNA and RNA Based Therapeutics," Feb. 2–3, 1998, Coronado, Calif.). Moore and Sharpe, Science 256:922 (1992), describe circularization of RNA using a DNA "splint."

It would be useful to improve the efficiency of RNA detection and amplification techniques involving ligation.

It is therefore an object of the present invention to provide techniques to allow ligation-mediated detection of RNA sequences.

It is a further object of the present invention to provide techniques to allow ligation-mediated amplification of RNA sequences.

It is a further object of the present invention to provide techniques to allow ligation-dependent detection of RNA sequences.

It is a further object of the present invention to provide techniques to allow ligation-dependent amplification of RNA sequences.

It is a further object of the present invention to provide techniques to allow ligation-mediated or ligation-dependent amplification and detection of RNA sequences.

It is a further object of the present invention to provide techniques to allow ligation-mediated or ligation-dependent amplification and detection of RNA sequences for the purpose of quantitative analysis of RNA expression levels.

BRIEF SUMMARY OF THE INVENTION

Disclosed are techniques for detection of nucleic acids, amplification of nucleic acids, or both, involving ligation by T4 RNA ligase of DNA strands hybridized to an RNA strand. These techniques are particularly useful for the detection of RNA sequences and for amplification of nucleic acids from, or dependent on, RNA sequences. Many known ligation-based detection and amplification techniques are improved through the use of T4 RNA ligase acting on DNA strands or ends. Such techniques include ligase chain reaction (LCR), ligation combined with reverse transcription polymerase chain reaction (RT PCR), ligation-mediated polymerase chain reaction (LMPCR), polymerase chain reaction/ligation detection reaction (PCR/LDR), ligation-dependent polymerase chain reaction (LD-PCR), oligo-nucleotide ligation assay (OLA), ligation-during-amplification (LDA), ligation of padlock probes, open circle probes, and other circularizable probes, and iterative gap ligation (IGL).

A preferred technique is the target-mediated ligation of open circle probes (see U.S. Pat. No. 5, 854,033 to Lizardi; also known as padlock probes; see Nilsson et al., Science 265:2085–2088 (1994)) where the target nucleic acid is RNA. This can be followed by rolling circle amplification (RCA) of the ligated open circle probe resulting in target-dependent nucleic acid amplification. Exponential rolling circle amplification (ERCA) can provide even more amplification.

It has been discovered that T4 RNA ligase can efficiently ligate DNA ends of nucleic acid strands hybridized to an RNA strand. In particular, this ligation is more efficient than the same ligation carried out with T4 DNA ligase. Thus, techniques involving ligation of DNA ends of nucleic acid strands hybridized to RNA can be performed more efficiently by using T4 RNA ligase.

DETAILED DESCRIPTION OF THE INVENTION

Figure 1:
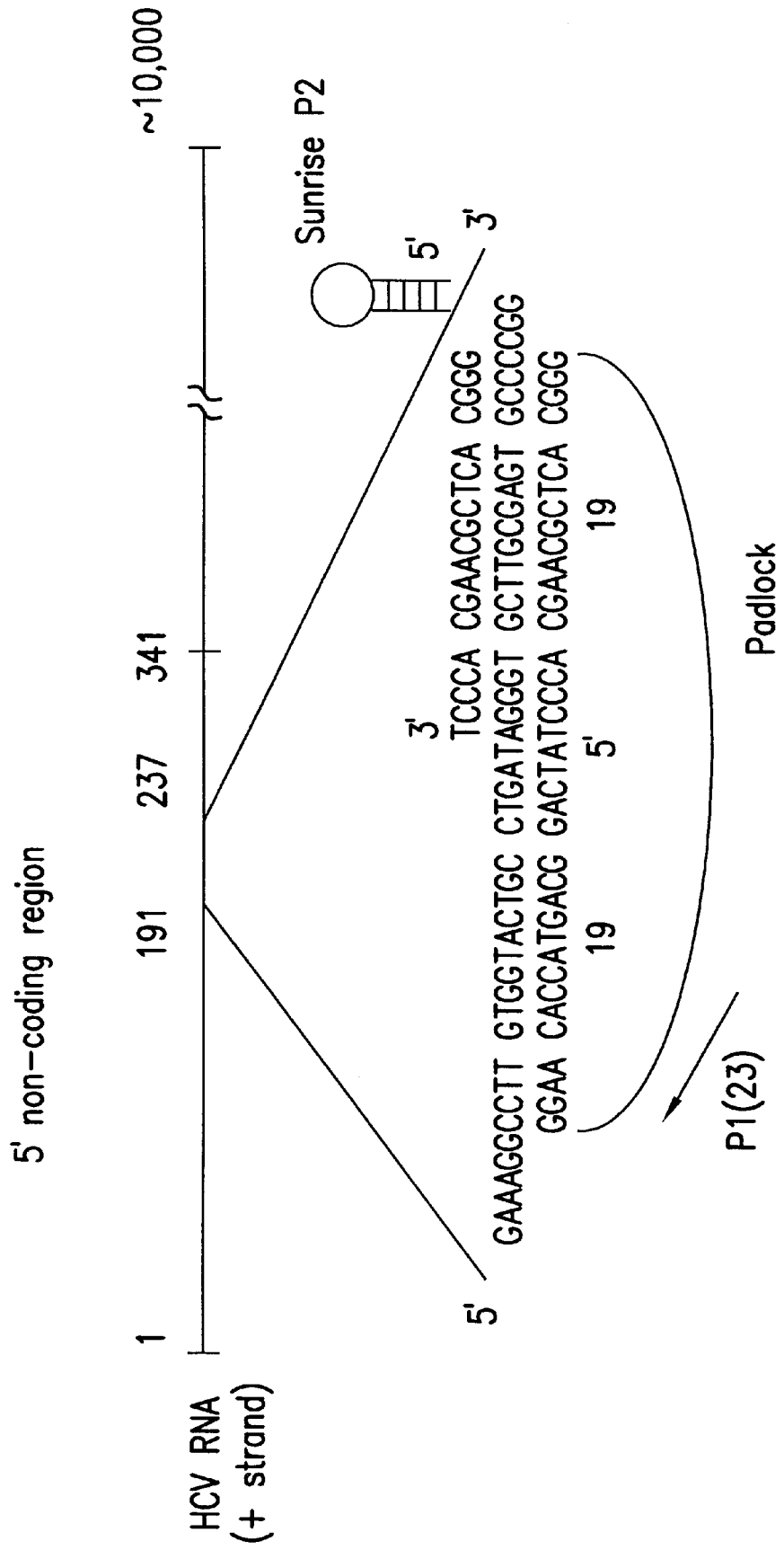
FIG. 1 is a diagram of the source and sequence of HCV RNA used as the synthetic target (47 nt). Only the plus strand RNA sequence is shown, the minus strand RNA sequence is complementary to the plus strand. Also shown are the sequences of the target probe portions of the open circle probe annealing to the target to form a nick, the position where Primer 1 hybridizes to the spacer portion of the open circle probe, and the sequence and hybridization location of Sunrise (SR) primer 2 used for the ERCA reaction.

The disclosed techniques involve the use of T4 RNA ligase. It has been discovered that T4 RNA ligase can efficiently ligate DNA ends of nucleic acid strands hybridized to an RNA strand. Surprisingly, this ligation is more efficient than the same ligation carried out with T4 DNA ligase. Thus, techniques involving ligation of DNA ends of nucleic acid strands hybridized to RNA can be performed more efficiently by using T4 RNA ligase. This discovery allows for the first time effective use of DNA probes, primers, and oligonucleotides hybridized to RNA where the technique involves ligation. The example specifically demonstrates that ligation of the ends of DNA strands hybridized to an RNA strand is effective and efficient. The same procedure using T4 DNA ligase would be significantly less effective.

Disclosed are techniques for detection of nucleic acids, amplification of nucleic acids, or both, involving ligation by T4 RNA ligase of DNA strands hybridized to an RNA strand. These techniques are particularly useful for the detection of RNA sequences and for amplification of nucleic acids from, or dependent on, RNA sequences. Many known ligation-based detection and amplification techniques are improved through the use of T4 RNA ligase acting on DNA strands or ends. Such techniques include ligase chain reaction (LCR; Wiedmann et al., *PCR Methods Appl.* 3(4):S51–64 (1994); Lee, Biologicals 24(3):197–199 (1996); Laffler et al., *Ann Biol Clin* (Paris) 51(9):821–826 (1993); U.S. Pat. No. 5,516,663 to Backman et al.), ligation combined with reverse transcription polymerase chain reaction (RT PCR; U.S. Pat. No. 5,187,060 to Cerruti et al.), ligation-mediated polymerase chain reaction (LMPCR; Becker and Mahler, *Antisense Nucleic Acid Drug Dev.* 9:313–319 (1999); Rodriguez and Akman, *Electrophoresis* 19:646–652 (1998)), polymerase chain reaction/ligation detection reaction (PCR/LDR, Zirvi et al., *Nucleic Acids Res.* 27:e40 (1999); U.S. Pat. No. 6,027,889 to Barany et al.; U.S. Pat. No. 5,912,148 to Eggerding), ligation-dependent polymerase chain reaction (LD-PCR; Park et al., *Am J Pathol* 149(5):1485–1491 (1996)), oligonucleotide ligation assay (OLA; Tobe et al., Nucleic Acids Res. 24:3728–3732 (1996); Gasparini et al., *J. Med. Screen.* 6:67–69 (1999)), ligation-during-amplification (LDA; Chen and Ruffner, *Nucleic Acids Res.* 26:1126–1127 (1998)), ligation of padlock probes (Nilsson et al., *Science* 265:2085–2088 (1994); Baner et al., *Nucleic Acids Res.* 26:5073–5078 (1998); Thomas et al., *Arch. Pathol Lab. Med.* 123:1170–1176 (1999)), open circle probes (U.S. Pat. No. 5, 854,033 to Lizardi), and other circularizable probes (Zhang et al., Gene 211:277–285 (1998)), iterative gap ligation (IGL; Stewart et al., *Nucleic Acids Res.* 26:961–966 (1998)), and other techniques involving ligation (Stefano et al., *Mol. Cell Probes* 11:407–426 (1997); U.S. Pat. No. 6,025,139 to Yager et al.; U.S. Pat. No. 6,020,138 to Akhaven-Tafti; U.S. Pat. No. 5,998,175 to Akhaven-Tafti; U.S. Pat. No. 5,962,223 to Whiteley et al.; U.S. Pat. No. 5,959,095 to Martinelli et al.; U.S. Pat. No. 5,942,609 to Hunkapiller et al.; U.S. Pat. No. 5,888,731 to Yager et al.; U.S. Pat. No. 5,871,914 to Nathan; U.S. Pat. No. 5,800,994 to Martinelli et al.; U.S. Pat. No. 5,770,408 to Sato).

These methods can be adapted for use with the disclosed method by using DNA forms of the probes, primers, oligonucleotides, or strands to be ligated, using RNA as the hybridization substrate for the DNA probes, primers, oligonucleotides, or strands to be ligated, and using T4 RNA ligase to perform the ligation.

A preferred technique is the target-mediated ligation of open circle probes where the target nucleic acid is RNA. This can be followed by rolling circle amplification (RCA) of the ligated open circle probe resulting in target-dependent nucleic acid amplification. Exponential rolling circle amplification (ERCA) can provide even more amplification.

Materials

A. T4 RNA Ligase

The disclosed method uses T4 RNA ligase. It has been discovered that T4 RNA ligase can efficiently ligate DNA ends of nucleic acid strands hybridized to an RNA strand. T4 RNA ligase is well characterized and is commercially available.

B. DNA Probes

The disclosed method involves the ligation of two nucleic acid strands while they are hybridized to an RNA strand. The nucleic acid strands to be ligated are referred to herein as DNA probes critical aspect of the disclosed DNA probes is that the 3'- and 5'-terminal nucleotides of the DNA probes be deoxyribonucleotides.

Reference to the nucleic acid molecules to be ligated as DNA probes is merely for ease of reference and is not intended to require that the strands be used as probes. It is understood that the various methods in which the disclosed DNA probes are ligated variously require that the ligated strands serve as probes, primers, detectable tags, substrates for nucleic acid amplification, capture or immobilization moieties, and numerous other functions. In general, the design of the DNA probes (that is, the strands to be ligated) will follow the requirements of the method being adapted, such requirements are known in the art. The critical aspect of the disclosed DNA probes is that the 3'- and 5'- terminal nucleotides of the DNA probes be deoxyribonucleotides.

The right and left probes can be part of a single molecule, such as an oligonucleotide, with each probe serving as one of ends of the molecule. A preferred example is an open circle probe where the right target probe portion is the right probe and the left target probe portion is the left probe. Open circle probes are described in detail in the section on rolling circle amplification.

C. RNA Targets

As used herein, an RNA target is an RNA molecule to which the disclosed DNA probes are hybridized for ligation. Any RNA molecule can be used as an RNA target in the disclosed method. Preferred RNA targets are naturally occurring RNA molecules such as mRNA, viral RNA, and ribosomal RNA.

The target RNA can come from any source. For example, target RNA can be obtained from mRNA samples, nucleic acid libraries, cells, cultures, tissues, bodily fluids, urine, serum, biopsy samples, and environmental samples. Numerous other sources of RNA are known or can be developed and any can be used with the disclosed method. Any RNA sample can be used as a target sample in the disclosed method. Examples of suitable target samples include mRNA samples, nucleic acid libraries, whole cell samples, environmental samples, culture samples, tissue samples, bodily fluids, urine samples, serum samples, and biopsy samples. Numerous other sources of target samples are known or can be developed and any can be used with the disclosed method.

D. Solid State DNA Probes

The DNA probes can be coupled to a substrate. Doing so is useful for a variety of purposes including capture of other DNA probes (via ligation), immobilization of the reaction or reaction products, allowing easy washing of reagents and reactions during an assay, and aiding identification or detection of ligated probes.

Solid-state substrates to which DNA probes can be attached can include any solid material to which oligonucleotides can be coupled, directly or indirectly. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. Preferred forms for solid-state substrates flat surfaces and beads, especially magnetic beads.

Methods for immobilization of oligonucleotides to solid-state substrates are well established. DNA probes can be coupled to substrates using established coupling methods. For example, suitable attachment methods are described by Pease et al., *Proc. Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Methods for producing arrays of oligonucleotides on solid-state substrates are also known. Examples of such techniques are described in U.S. Patent No. 5,871,928 to Fodor et al., U.S. Pat. No. 5,54,413, U.S. Pat. No. 5,429,807, and U.S. Pat. No. 5,599,695 to Pease et al.

Although preferred, it is not required that a given array of DNA probes be a single unit or structure. The set of probes may be distributed over any number of solid supports. For example, at one extreme, each probe may be immobilized in a separate reaction tube, container, or bead.

E. Solid State Targets

The RNA targets can be coupled to a substrate. Doing so is useful for a variety of purposes including immobilization of the reaction or reaction products, allowing easy washing of reagents and reactions during an assay, aiding identification or detection of ligated probes, and making it easier to assay multiple samples simultaneously.

Solid-state substrates to which RNA targets can be attached can include any solid material to which nucleic acids can be attached, adhered, or coupled, either directly or indirectly. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. Preferred forms for solid-state substrates flat surfaces and beads, especially magnetic beads.

Methods for immobilization of nucleic acids to solid-state substrates are well established. In general, RNA targets can be immobilized on a substrate as part of a nucleic acid sample or other sample containing RNA targets. RNA targets can be coupled to substrates using established coupling methods. For example, suitable attachment methods are described by Pease et al., *Proc. Natl. Acad Sci. USA* 91(11):5022–5026 (1994), Guo et al., *Nucleic Acids Res.* 22:5456–5465 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995).

Methods for producing arrays of nucleic acids on solid-state substrates are also known. Examples of such techniques are described in U.S. Pat. Nos. 5,871,928 to Fodor et al., U.S. Pat. No. 5,54,413, U.S. Pat. No. 5,429,807, and U.S. Pat. No. 5,599,695 to Pease et al. Microarrays of RNA targets can be fabricated, for example, using the method described by Schena et al., *Science* 270:487–470 (1995).

Although preferred, it is not required that a given array of RNA targets be a single unit or structure. The set of probes may be distributed over any number of solid supports. For example, at one extreme, each RNA target or each nucleic acid sample may be immobilized in a separate reaction tube, container, or bead.

F. Detection Labels

To aid in detection and quantitation of ligated DNA probes, labels can be incorporated into, or coupled to, DNA probes. A label is any molecule that can be associated with DNA probes, directly or indirectly, and which results in a measurable, detectable signal, either directly or indirectly. Many such labels for incorporation into nucleic acids or coupling to nucleic acids are known. Examples of labels suitable for use in the disclosed method are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

Labeled nucleotides are a preferred form of label since they can be directly incorporated into DNA probes during synthesis. Examples of labels that can be incorporated into DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluoresceinisothiocyanate-dUTP, Cyanine-3-dUTP and Cyanine-5-dUTP (Yu et al., *Nucleic Acids Res.,* 22:3226–3232 (1994)). A preferred nucleotide analog detection label for DNA is BrdUrd (BUDR triphosphate, Sigma), and a preferred nucleotide analog detection label for RNA is Biotin- 16-uridine-5'-triphosphate (Biotin- 16-dUTP, Boehringer Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'chloro)tricyclo [3.3.1.1$^{3,7}$]decane]-4-yl) phenyl phosphate; Tropix, Inc.).

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled.

G. Capture Tags

A capture tag is any compound that can be used to separate compounds or complexes having the capture tag from those that do not. Preferably, a capture tag is a compound, such as a ligand or hapten, that binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

Preferred capture tags, described in the context of nucleic acid probes, are described by Syvnen et al., *Nucleic Acids Res.*, 14:5037 (1986). Preferred capture tags include biotin, which can be incorporated into nucleic acids. In the disclosed method, capture tags incorporated into DNA probes or RNA targets can allow the probes or targets to be captured, adhered to, or coupled to a substrate. Such capture allows simplified washing and handling of the probes and targets, and allows automation of all or part of the method. Capture tags can also be used with other specific components in certain embodiments of the disclosed method.

Capturing DNA probes or RNA targets on a substrate may be accomplished in several ways. In one embodiment, capture docks are adhered or coupled to the substrate. The capture docks mediate adherence of a probe or target by binding to, or interacting with, a capture tag on the probe or target. Capture docks immobilized on a substrate allow capture of the probe or target on the substrate. Such capture provides a convenient means of washing away reaction components that might interfere with subsequent steps.

Substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Preferred forms of substrates are plates and beads. The most preferred form of beads are magnetic beads.

In one embodiment, the capture dock is an oligonucleotide. Methods for immobilizing and coupling oligonucleotides to substrates are well established. For example, suitable attachment methods are described by Pease et al., *Proc. Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad Sci. USA* 92:6379–6383 (1995). A preferred method of attaching oligonucleotides to solid-state substrates is described by Guo et al., *Nucleic Acids Res.* 22:5456–5465 (1994).

In another embodiment, the capture dock is the anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Methods

The disclosed method involves detection of nucleic acids, amplification of nucleic acids, or both, through ligation by T4 RNA ligase of DNA strands hybridized to an RNA strand. These techniques are particularly useful for the detection of RNA sequences and for amplification of nucleic acids from, or dependent on, RNA sequences.

Many known ligation-based detection and amplification techniques are improved through the use of T4 RNA ligase acting on DNA strands or ends. Such techniques include ligase chain reaction (LCR; Wiedmann et al., *PCR Methods Appl.* 3(4):S51–64 (1994); Lee, *Biologicals* 24(3):197–199 (1996); Lafller et al., *Ann Biol Clin* (*Paris*) 51(9):821–826 (1993); U.S. Pat. No. 5,516,663 to Backman et al.), ligation combined with reverse transcription polymerase chain reaction (RT PCR; U.S. Pat. No. 5,187,060 to Cerruti et al.), ligation-mediated polymerase chain reaction (LMPCR; Becker and Mahler, *Antisense Nucleic Acid Drug Dev.*

9:313–319 (1999); Rodriguez and Akman, *Electrophoresis* 19:646–652 (1998)), polymerase chain reaction/ligation detection reaction (PCR/LDR; Zirvi et al., *Nucleic Acids Res.* 27:e40 (1999); U.S. Pat. No. 6,027,889 to Barany et al.; U.S. Pat. No. 5,912,148 to Eggerding), ligation-dependent polymerase chain reaction (LD-PCR; Park et al., *Am J Pathol* 149(5):1485–1491 (1996)), oligonucleotide ligation assay (OLA; Tobe et al., Nucleic Acids Res. 24:3728–3732 (1996); Gasparini et al., *J Med. Screen.* 6:6769–69 (1999)), ligation-during-amplification (LDA; Chen and Ruffner, *Nucleic Acids Res.* 26:1126–1127 (1998)), ligation of padlock probes (Nilsson et al., Science 265:2085–2088 (1994); Baner et al., *Nucleic Acids Res.* 26:5073–5078 (1998); Thomas et al., *Arch. Pathol. Lab. Med.* 123:1170–1176 (1999)), open circle probes (U.S. Pat. No. 5, 854,033 to Lizardi), and other circularizable probes (Zhang et al., *Gene* 211:277–285 (1998)), iterative gap ligation (IGL; Stewart et al., *Nucleic Acids Res.* 26:961–966 (1998)), and other techniques involving ligation (Stefano et al., *Mol. Cell Probes* 11:407–426 (1997); U.S. Pat. Nos. 6,025,139 to Yager et al.; 6,020,138 to Akhaven-Tafti; 5,998,175 to Akhaven-Tafti; 5,962,223 to Whiteley et al.; 5,959,095 to Martinelli et al.; 5,942,609 to Hunkapiller et al.; 5,888,731 to Yager et al.; 5,871,914 to Nathan; 5,800,994 to Martinelli et al.; 20 5,770,408 to Sato).

A. Ligase Chain Reaction

One mechanism for target amplification involving ligation is known as ligase chain reaction (LCR; Wiedmann et al., *PCR Methods Appl.* 3(4):S51–64 (1994); Lee, *Biologicals* 24(3):197–199 (1996); Laffler et al., *Ann Biol Clin (Paris)* 51(9):821–826 (1993)). In LCR, two primary probes (first and second, both of same sense) and two secondary probes (third and fourth, both of opposite sense with respect to primary probes) are employed in excess. The first probe hybridizes to a first segment of the target strand and the second probe hybridizes to a second segment of the target strand, the first and second segments being contiguous so that the 3' hydroxyl end of an"upstream" probe abuts the 5' phosphate end of a "downstream" probe, and so that a ligase can covalently ligate the two probes into a fused ligation product.

In like manner, LCR employs upstream and downstream secondary probes. A third probe (downstream secondary) can hybridize to the first probe (upstream primary) and a fourth probe (upstream secondary) can hybridize to the second probe (downstream primary) in a similar abutting fashion. Once the fused strand of primary probes is separated from the target strand, it will hybridize with the third and fourth (secondary) probes which can be ligated to form a complementary, secondary fused product. The fused products are functionally equivalent to either the target or its complement. By repeated cycles of hybridization and ligation, amplification of the target sequence is achieved. LCR is described more completely in EP-A-320 308.

A modified form of ligase chain reaction is described in U.S. Pat. No. 5,516,663 to Backman. The modified LCR method involves, in an LCR method, using an upstream probe having a 3' end modification such that the probe is incapable of ligation to its downstream partner. The 3' end modification is correctable only when the modified probe is hybridized to the target sequence. The modified probe is hybridized to the target, if present, to form a modified probe-template complex. The modification is then corrected in a target-dependent manner using endonuclease IV to create a 3' hydroxyl end. This correction allows the corrected probe to be ligated to its downstream partner. The corrected probe is then ligated to its downstream partner to form an amplification product. The amplification product is then dissociated from the target and the cycle of hybridization, correction, and ligation is repeated to amplify the target sequence.

Ligase chain reaction can be adapted for the disclosed method by using DNA LCR probes (or LCR probes with terminal deoxyribonucleotides), RNA target sequences, and T4 RNA ligase to ligate the probes on the RNA target. The LCR probes can also be RNA.

B. Ligation and Polymerase Chain Reaction

Reverse transcription polymerase chain reaction (RT-PCR; U.S. Pat. No. 5,187,060 to Cerruti et al.) has been used to detect target RNA sequences. This can be combined with ligation of binary probes hybridized to the RNA prior to reverse transcription, thus adding an additional discrimination step. Ligation-dependent PCR (LD-PCR; Park et al., *Am J Pathol* 149(5):1485–1491 (1996); Hsuih et al., *J Clin Microbiol* 34(3):501–7 (1996)) uses two hemiprobes hybridized to target RNA. The hemiprobes are then ligated by ligase to form a full probe that serves as a PCR primer. Capture probes hybridized to the RNA can be used for isolation. The hybrids are isolated through binding of the capture probes to paramagnetic beads.

Forms of PCR and RT PCR involving ligation can be adapted for the disclosed method by using DNA probes (or probes with terminal deoxyribonucleotides) for the strands to be ligated (for example, as the hemiprobes), RNA target sequences, and T4 RNA ligase to ligate the probes on the RNA target.

C. Padlock Probes

Padlock probes are hybridization probes having sequences at each end that are complementary to adjacent regions in a target sequence. Upon hybridization to the target sequence, the ends of the padlock probe are ligated together thus circularizing the probe and topologically locking the probe to the target sequence. Unligated probes (generally probes that do not hybridize or that are imperfectly hybridized) can be washed away while ligated probes will not. Padlock probes combine hybridization and ligation to increase target discrimination. Padlock probes and their use are described in PCT Application WO 95/22623. The use of padlock probes can be adapted for the disclosed method by using DNA padlock probes (or padlock probes with terminal deoxyribonucleotides), RNA target sequences, and T4 RNA ligase to circularize the padlock probe on the RNA target.

D. Rolling Circle Amplification

A preferred technique is the target-mediated ligation of open circle probes (see U.S. Pat. No. 5, 854,033 to Lizardi; also known as padlock probes; see Nilsson et al., *Science* 265:2085–2088 (1994)) where the target nucleic acid is RNA. This can be followed by rolling circle amplification (RCA) of the ligated open circle probe resulting in target-dependent nucleic acid amplification. Exponential rolling circle amplification (ERCA) can provide even more amplification.

Rolling circle amplification can be adapted for the disclosed method by using DNA open circle probes (or open circle probes with terminal deoxyribonucleotides), RNA target sequences, and T4 RNA ligase to circularize the open circle probe on the RNA target. Rolling circle replication generally requires that the open circle probe be composed entirely of deoxyribonucleotides, so use of DNA open circle probes does not affect RCA.

In RCA, a rolling circle replication primer hybridizes to circular OCP or ATC molecules followed by rolling circle replication of the OCP or ATC molecules using a strand-displacing DNA polymerase. Amplification takes place during rolling circle replication in a single reaction cycle. Rolling circle replication results in large DNA molecules containing tandem repeats of the OCP or ATC sequence. This DNA molecule is referred to as a tandem sequence DNA (TS-DNA). Rolling circle amplification is also referred to herein as unimolecular segment amplification (USA). The term unimolecular segment amplification is generally used herein to emphasis the amplification of individual segments of nucleic acid, such as a target sequence, that are of interest.

A preferred embodiment, ligation-mediated rolling circle amplification (LM-RCA) method involves a ligation operation prior to replication. In the ligation operation, an OCP hybridizes to its cognate target nucleic acid sequence (in the RNA target), if present, followed by ligation of the ends of the hybridized OCP to form a covalently closed, single-stranded OCP. After ligation, a rolling circle replication primer hybridizes to OCP molecules followed by rolling circle replication of the circular OCP molecules using a strand-displacing DNA polymerase. Generally, LM-RCA comprises (a) mixing an open circle probe (OCP) with a target sample, resulting in an OCP-target sample mixture, and incubating the OCP-target sample mixture under conditions promoting hybridization between the open circle probe and a target sequence, (b) mixing ligase with the OCP-target sample mixture, resulting in a ligation mixture, and incubating the ligation mixture under conditions promoting ligation of the open circle probe to form an amplification target circle (ATC), (c) mixing a rolling circle replication primer (RCRP) with the ligation mixture, resulting in a primer-ATC mixture, and incubating the primer-ATC mixture under conditions that promote hybridization between the amplification target circle and the rolling circle replication primer, (d) mixing DNA polymerase with the primer-ATC mixture, resulting in a polymerase-ATC mixture, and incubating the polymerase-ATC mixture under conditions promoting replication of the amplification target circle, where replication of the amplification target circle results in formation of tandem sequence DNA (TS-DNA).

The open circle probe is a single-stranded, linear DNA molecule comprising, from 5' end to 3' end, a 5' phosphate group, a right target probe portion, a primer complement portion, a spacer region, a left target probe portion, and a 3' hydroxyl group, wherein the left target probe portion is complementary to the 5' region of a target sequence and the right target probe portion is complementary to the 3' region of the target sequence.

The left and right target probe portions hybridize to the two ends of the target nucleic acid sequence, with or without a central gap to be filled by one or more gap oligonucleotides. Generally, LM-RCA using gap oligonucleotides can be performed by, in an LM-RCA reaction, (1) using a target sequence with a central region located between a 5' region and a 3' region, and an OCP where neither the left target probe portion of the open circle probe nor the right target probe portion of the open circle probe is complementary to the central region of the target sequence, and (2) mixing one or more gap oligonucleotides with the target sample, such that the OCP-target sample mixture contains the open circle probe, the one or more gap oligonucleotides, and the target sample, where each gap oligonucleotide consists of a single-stranded, linear DNA molecule comprising a 5' phosphate group and a 3' hydroxyl group, where each gap oligonucleotide is complementary all or a portion of the central region of the target sequence.

1. The Ligation Operation

An open circle probe, optionally in the presence of one or more gap oligonucleotides, is incubated with a sample containing RNA under suitable hybridization conditions, and then ligated to form a covalently closed circle using T4 RNA ligase. The ligated open circle probe is a form of amplification target circle. This operation is similar to ligation of padlock probes described by Nilsson et al., *Science*, 265:2085–2088 (1994). The ligation operation allows subsequent amplification to be dependent on the presence of a target sequence. The ligase and ligation conditions can be optimized to limit the frequency of ligation of single-stranded termini. Such ligation events do not depend on the presence of a target sequence.

2. The Replication Operation

The circular open circle probes formed by specific ligation and amplification target circles serve as substrates for a rolling circle replication. This reaction requires the addition of two reagents: (a) a rolling circle replication primer, which is complementary to the primer complement portion of the OCP or ATC, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 1000 tandem copies of a sequence complementary to the amplification target circle or open circle probe. This tandem sequence DNA (TS-DNA) consists of, in the case of OCPs, alternating target sequence and spacer sequence. Note that the spacer sequence of the TS-DNA is the complement of the sequence between the left target probe and the right target probe in the original open circle probe. A preferred rolling circle DNA polymerase is the DNA polymerase of the bacteriophage φ29.

During rolling circle replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Rolling circle amplification can be engineered to produce TS-DNA of different lengths in an assay involving multiple ligated OCPs or ATCs. This can be useful for extending the number of different targets that can be detected in a single assay. TS-DNA of different lengths can be produced in several ways. In one embodiment, the base composition of the spacer region of different classes of OCP or ATC can be designed to be rich in a particular nucleotide. Then a small amount of the dideoxy nucleotide complementary to the enriched nucleotide can be included in the rolling circle amplification reaction. After some amplification, the dideoxy nucleotides will terminate extension of the TS-DNA product of the class of OCP or ATC enriched for the complementary nucleotide. Other OCPs or ATCs will be less likely to be terminated, since they are not enriched for the complementary nucleotide, and will produce longer TS-DNA products, on average.

In another embodiment, two different classes of OCP or ATC can be designed with different primer complement portions. These different primer complement portions are designed to be complementary to a different rolling circle replication primer. Then the two different rolling circle replication primers are used together in a single rolling circle amplification reaction, but at significantly different concentrations. The primer at high concentration immediately primes rolling circle replication due to favorable kinetics, while the primer at lower concentration is delayed in priming due to unfavorable kinetics. Thus, the TS-DNA product of the class of OCP or ATC designed for the primer at high concentration will be longer than the TS-DNA product of the class of OCP or ATC designed for the primer at lower concentration since it will have been replicated for a longer period of time.

Additional forms of RCA are described in PCT Application WO 97/20948.

3. Open Circle Probes

An open circle probe (OCP) is a linear single-stranded DNA molecule, generally containing between 50 to 1000 nucleotides, preferably between about 60 to 150 nucleotides, and most preferably between about 70 to 100 nucleotides. The OCP has a 5' phosphate group and a 3' hydroxyl group. This allows the ends to be ligated using a DNA ligase, or extended in a gap-filling operation. Portions of the OCP have specific functions making the OCP useful for RCA and LM-RCA. These portions are referred to as the target probe portions, the primer complement portion, the spacer region, the detection tag portions, the secondary target sequence portions, the address tag portions, and the promoter portion. The target probe portions and the primer complement portion are required elements of an open circle probe. The primer complement portion is part of the spacer region. Detection tag portions, secondary target sequence portions, and promoter portions are optional and, when present, are part of the spacer region. Address tag portions are optional and, when present, may be part of the spacer region. Generally, an open circle probe is a single-stranded, linear DNA molecule comprising, from 5' end to 3' end, a 5' phosphate group, a right target probe portion, a spacer region, a left target probe portion, and a 3' hydroxyl group, with a primer complement portion present as part of the spacer region. Those segments of the spacer region that do not correspond to a specific portion of the OCP can be arbitrarily chosen sequences. It is preferred that OCPs do not have any sequences that are self-complementary. It is considered that this condition is met if there are no complementary regions greater than six nucleotides long without a mismatch or gap. It is also preferred that OCPs containing a promoter portion do not have any sequences that resemble a transcription terminator, such as a run of eight or more thymidine nucleotides.

The open circle probe, when ligated and replicated, gives rise to a long DNA molecule containing multiple repeats of sequences complementary to the open circle probe. This long DNA molecule is referred to herein as tandem sequences DNA (TS-DNA). TS-DNA contains sequences complementary to the target probe portions, the primer complement portion, the spacer region, and, if present on the open circle probe, the detection tag portions, the secondary target sequence portions, the address tag portions, and the promoter portion. These sequences in the TS-DNA are referred to as target sequences (which match the original target sequence), primer sequences (which match the sequence of the rolling circle replication primer), spacer sequences (complementary to the spacer region), detection tags, secondary target sequences, address tags, and promoter sequences.

A particularly preferred embodiment is an open circle probe of 70 to 100 nucleotides including a left target probe of 20 nucleotides and a right target probe of 20 nucleotides. The left target probe and right target probe hybridize to a target sequence leaving a gap of five nucleotides, which is filled by a single pentanucleotide gap oligonucleotide.

a. Target Probe Portions

There are two target probe portions on each OCP, one at each end of the OCP. The target probe portions can each be any length that supports specific and stable hybridization between the target probes and the target sequence. For this purpose, a length of 10 to 35 nucleotides for each target probe portion is preferred, with target probe portions 15 to 20 nucleotides long being most preferred. The target probe portion at the 3' end of the OCP is referred to as the left target probe, and the target probe portion at the 5' end of the OCP is referred to as the right target probe. These target probe portions are also referred to herein as left and right target probes or left and right probes. The target probe portions are complementary to a target nucleic acid sequence.

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation. Optionally, the 5' end and the 3' end of the target probe portions may hybridize in such a way that they are separated by a gap space. In this case the 5' end and the 3' end of the OCP may only be ligated if one or more additional oligonucleotides, referred to as gap oligonucleotides, are used, or if the gap space is filled during the ligation operation. The gap oligonucleotides hybridize to the target sequence in the gap space to a form continuous probe/target hybrid. The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase during the ligation operation. When using such a gap-filling operation, a gap space of three to five nucleotides in length is most preferred. As another alternative, the gap space can be partially bridged by one or more gap oligonucleotides, with the remainder of the gap filled using DNA polymerase.

b. Primer Complement Portion

The primer complement portion is part of the spacer region of an open circle probe. The primer complement portion is complementary to the rolling circle replication primer (RCRP). Each OCP should have a single primer complement portion. This allows rolling circle replication to initiate at a single site on ligated OCPs. The primer complement portion and the cognate primer can have any desired sequence so long as they are complementary to each other. In general, the sequence of the primer complement can be chosen such that it is not significantly similar to any other portion of the OCP. The primer complement portion can be any length that supports specific and stable hybridization between the primer complement portion and the primer. For this purpose, a length of 10 to 35 nucleotides is preferred, with a primer complement portion 16 to 20 nucleotides long being most preferred. The primer complement portion can be located anywhere within the spacer region of an OCP. It is preferred that the primer complement portion is adjacent to the right target probe, with the right target probe portion and the primer complement portion preferably separated by three to ten nucleotides, and most preferably separated by six nucleotides. This location prevents the generation of any other spacer sequences, such as detection tags and secondary target sequences, from unligated open circle probes during DNA replication.

c. Detection Tag Portions

Detection tag portions are part of the spacer region of an open circle probe. Detection tag portions have sequences matching the sequence of the complementary portion of detection probes. These detection tag portions, when amplified during rolling circle replication, result in TS-DNA having detection tag sequences that are complementary to the complementary portion of detection probes. If present, there may be one, two, three, or more than three detection tag portions on an OCP. It is preferred that an OCP have two, three or four detection tag portions. Most preferably, an OCP will have three detection tag portions. Generally, it is preferred that an OCP have 60 detection tag portions or less. There is no fundamental limit to the number of detection tag portions that can be present on an OCP except the size of the OCP. When there are multiple detection tag portions, they may have the same sequence or they may have different sequences, with each different sequence complementary to a different detection probe. It is preferred that an OCP contain detection tag portions that have the same sequence such that they are all complementary to a single detection probe. For some multiplex detection methods, it is preferable that OCPs contain up to six detection tag portions and that the detection tag portions have different sequences such that each of the detection tag portions is complementary to a different detection probe. The detection tag portions can each be any length that supports specific and stable hybridization between the detection tags and the detection probe. For this purpose, a length of 10 to 35 nucleotides is preferred, with a detection tag portion 15 to 20 nucleotides long being most preferred.

d. Secondary Target Sequence Portions

Secondary target sequence portions are part of the spacer region of an open circle probe. Secondary target sequence portions have sequences matching the sequence of target probes of a secondary open circle probe. These secondary target sequence portions, when amplified during rolling circle replication, result in TS-DNA having secondary target sequences that are complementary to target probes of a secondary open circle probe. If present, there may be one, two, or more than two secondary target sequence portions on an OCP. It is preferred that an OCP have one or two secondary target sequence portions. Most preferably, an OCP will have one secondary target sequence portion. Generally, it is preferred that an OCP have 50 secondary target sequence portions or less. There is no fundamental limit to the number of secondary target sequence portions that can be present on an OCP except the size of the OCP. When there are multiple secondary target sequence portions, they may have the same sequence or they may have different sequences, with each different sequence complementary to a different secondary OCP. It is preferred that an OCP contain secondary target sequence portions that have the same sequence such that they are all complementary to a single target probe portion of a secondary OCP. The secondary target sequence portions can each be any length that supports specific and stable hybridization between the secondary target sequence and the target sequence probes of its cognate OCP. For this purpose, a length of 20 to 70 nucleotides is preferred, with a secondary target sequence portion 30 to 40 nucleotides long being most preferred. As used herein, a secondary open circle probe is an open circle probe where the target probe portions match or are complementary to secondary target sequences in another open circle probe or an amplification target circle. It is contemplated that a secondary open circle probe can itself contain secondary target sequences that match or are complementary to the target probe portions of another secondary open circle probe. Secondary open circle probes related to each other in this manner are referred to herein as nested open circle probes.

e. Address Tag Portion

The address tag portion is part of either the target probe portions or the spacer region of an open circle probe. The address tag portion has a sequence matching the sequence of the complementary portion of an address probe. This address tag portion, when amplified during rolling circle replication, results in TS-DNA having address tag sequences that are complementary to the complementary portion of address probes. If present, there may be one, or more than one, address tag portions on an OCP. It is preferred that an OCP have one or two address tag portions. Most preferably, an OCP will have one address tag portion. Generally, it is preferred that an OCP have 50 address tag portions or less. There is no fundamental limit to the number of address tag portions that can be present on an OCP except the size of the OCP. When there are multiple address tag portions, they may have the same sequence or they may have different sequences, with each different sequence complementary to a different address probe. It is preferred that an OCP contain address tag portions that have the same sequence such that they are all complementary to a single address probe. Preferably, the address tag portion overlaps all or a portion of the target probe portions, and all of any intervening gap space. Most preferably, the address tag portion overlaps all or a portion of both the left and right target probe portions. The address tag portion can be any length that supports specific and stable hybridization between the address tag and the address probe. For this purpose, a length between 10 and 35 nucleotides long is preferred, with an address tag portion 15 to 20 nucleotides long being most preferred.

f. Promoter Portion

The promoter portion corresponds to the sequence of an RNA polymerase promoter. A promoter portion can be included in an open circle probe so that transcripts can be generated from TS-DNA. The sequence of any promoter may be used, but simple promoters for RNA polymerases without complex requirements are preferred. It is also preferred that the promoter is not recognized by any RNA polymerase that may be present in the sample containing the target nucleic acid sequence. Preferably, the promoter portion corresponds to the sequence of a T7 or SP6 RNA polymerase promoter. The T7 and SP6 RNA polymerases are highly specific for particular promoter sequences. Other promoter sequences specific for RNA polymerases with this characteristic would also be preferred. Because promoter sequences are generally recognized by specific RNA polymerases, the cognate polymerase for the promoter portion of the OCP should be used for transcriptional amplification. Numerous promoter sequences are known and any promoter specific for a suitable RNA polymerase can be used. The promoter portion can be located anywhere within the spacer region of an OCP and can be in either orientation. Preferably, the promoter portion is immediately adjacent to the left target probe and is oriented to promote transcription toward the 3' end of the open circle probe. This orientation results in transcripts that are complementary to TS-DNA, allowing independent detection of TS-DNA and the transcripts, and prevents transcription from interfering with rolling circle replication.

4. Gap Oligonucleotides

Gap oligonucleotides are oligonucleotides that are complementary to all or a part of that portion of a target sequence which covers a gap space between the ends of a hybridized open circle probe. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized open circle probe can be filled with a single gap oligonucleotide, or it can be filled with multiple gap oligonucleotides. For example, two 3 nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic variants of a target sequence. By placing the region of the target sequence in which the variation occurs in the gap space formed by an open circle probe, a single open circle probe can be used to amplify each of the individual variants by using an appropriate set of gap oligonucleotides.

5. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. Ligated open circle probes are a type of ATC, and as used herein the term amplification target circle includes ligated open circle probes. An ATC can be used in the same manner as described herein for OCPs that have been ligated.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

6. Rolling Circle Replication Primer

A rolling circle replication primer (RCRP) is an oligonucleotide having sequence complementary to the primer complement portion of an OCP or ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the OCP or ATC. The complementary portion of a rolling circle replication primer can be any length that supports specific and stable hybridization between the primer and the primer complement portion. Generally this is 10 to 35 nucleotides long, but is preferably 16 to 20 nucleotides long.

It is preferred that rolling circle replication primers also contain additional sequence at the 5' end of the RCRP that is not complementary to any part of the OCP or ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. The rolling circle replication primer may also include modified nucleotides to make it resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. A rolling circle replication primer can be used as the tertiary DNA strand displacement primer in strand displacement cascade amplification.

EXAMPLE

Exponential RCA was performed using T4 RNA ligase to ligate an open circle probe to HCV RNA sequence used as the synthetic target (47 nt). The relationship of the components used is shown in FIG. 1. Only the plus strand RNA sequence is shown, minus strand RNA sequence will be complementary to the plus strand. FIG. 1 also shows the padlock arm sequences annealing to the target to form a nick. Also shown is the position of Primer 1 and the Sunrise (SR) primer 2 used for the ERCA reaction.

Figure 2:
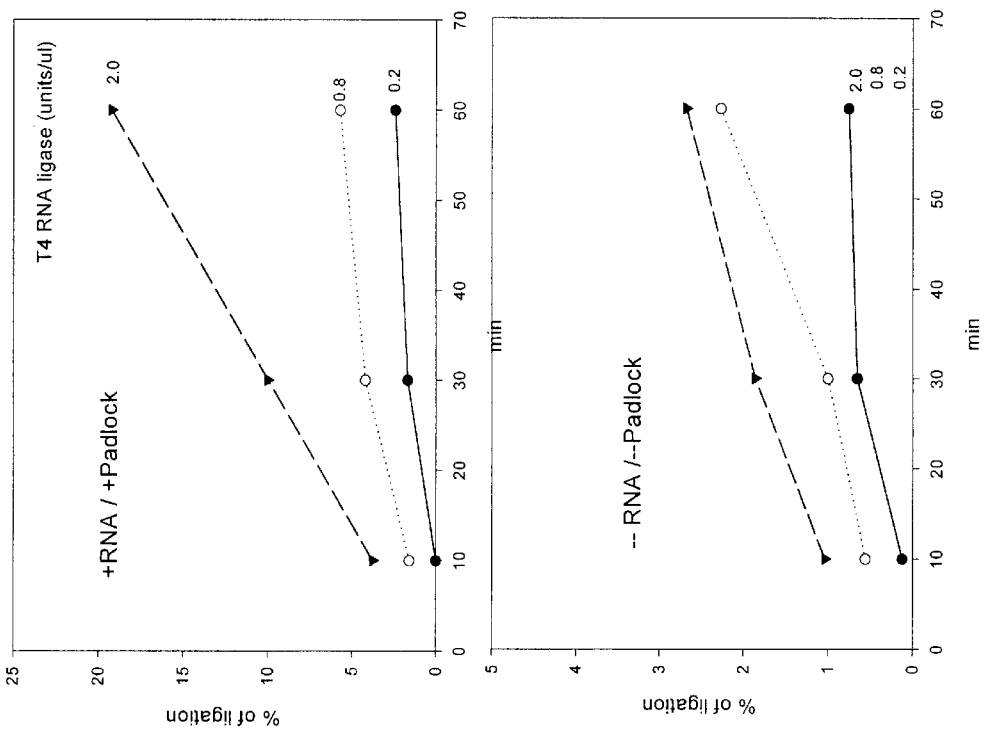
FIG. 2 shows graphs of the progress of ligation (expressed as the percent of molecules ligated) over time (in minutes).

DNA padlocks were 5' end labeled with $\gamma$-$^{32}$P. Labeled padlocks (10 nM) and synthetic RNA targets (20 nM) were denatured at 95° C. and allowed to anneal over time in 1×T4 RNA ligase buffer (50 mM Tris-HCl (pH 7.8), 10 mM $MgCl_2$, 10 mM dithiothreitol, and 1 mM ATP). The annealed mixture (50 µl) was incubated at 37° C. with varying concentrations of T4 RNA ligase and for varying times. The reactions were run on 8% denaturing PAGE gel. DNA padlocks were able to ligate on the synthetic RNA templates to form circular padlocks. There was an increase in padlock formation up to 60 minutes. Overnight ligation did not give any appreciable increase over 60 minutes. Only the matched padlock/RNA combinations (+/+ and −/−) gave any ligation. Mismatched padlock/RNA combinations (+/−) did not show any ligation. The matched padlock/RNA combination (+/+) gave 20% ligation whereas the (−/−) padlock/RNA combination gave only 3% ligation at 2 units/µl of T4 RNA ligase (FIG. 2). Thus, T4 RNA ligase efficiently ligated the DNA padlocks when hybridized to an RNA strand.

Figure 3:
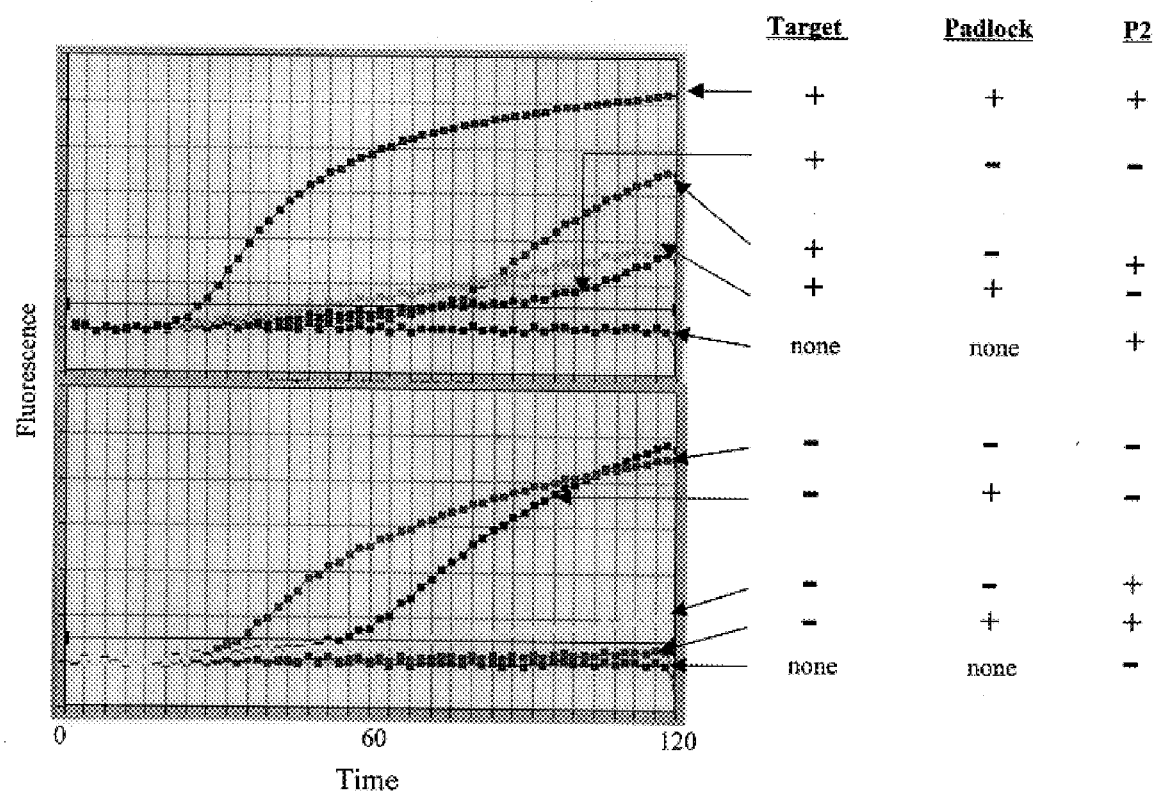
FIG. 3 is a graph of fluorescence generated by ERCA over time (in minutes) using various combinations of target, open circle probe, and primer.

Ligations were carried out as above without end labeling of DNA padlocks with $^{32}$P. One-tenth of the ligation reaction was used in an ERCA reaction (30 µl) containing 20 mM Tris-HCl, 10 mM KCl, 10 mM $(NH_4)_2SO_4$, 2 mM $MgSO_4$, 0.1% Triton X-100 (pH 8.8 at 25° C.). In addition, reactions contained 400 uM deoxyribonucleoside triphosphates, 8 units Bst DNA polymerase and 1 µM each of primer 1 and SR primer 2. The Real-Time ERCA reactions were run in the ABI PRISM 7700 instrument at 65° C. for 2 hours. As seen in FIG. 3, specific amplification was observed in the case of matching padlock/RNA combinations (+/+ and −/−). However, some non-specific signal was observed with unmatched padlock/RNA combinations, which came up several minutes after the specific signal.

Figure 4:
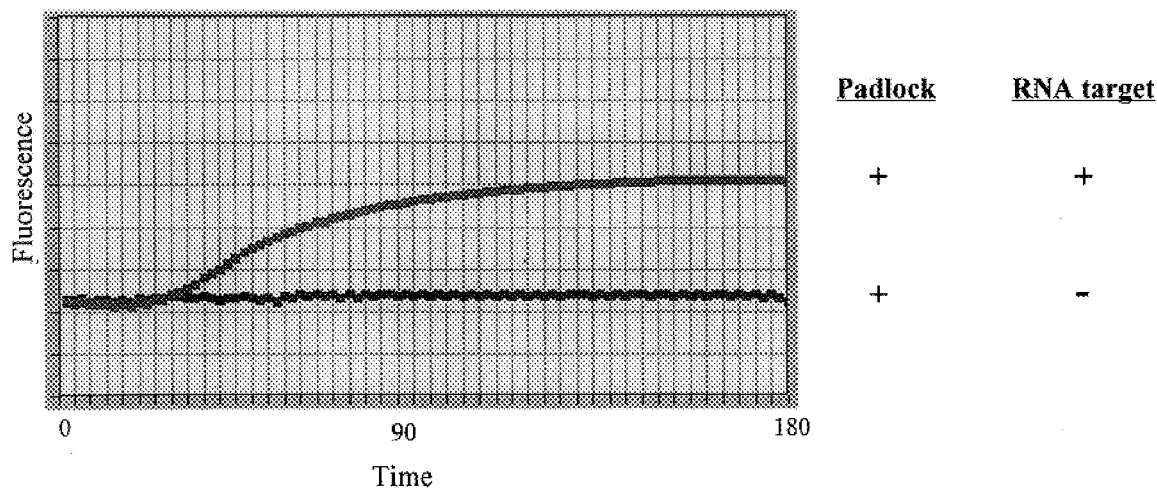
FIG. 4 is a graph of fluorescence generated by ERCA over time (in minutes) in the presence of 10% formamide. The results of two assays are graphed: one in the presence and one in the absence of RNA target.

In order to reduce the non-specific signal, 10% formamide was included in the ligation reaction with T4 RNA ligase. Real-Time ERCA reactions were carried out as described above with these ligations. As shown in FIG. 4, addition of 10% formamide in the ligation reaction eliminated the non-specific signal observed with unmatched padlock/RNA (+/+) leaving the specific signal.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

wherein the right probe and the left probe are designed to hybridize to a target sequence such that the 5' end of the right probe and the 3' end of the left probe are adjacent and can be ligated, wherein at least the 5'-terminal nucleotide of the right probe and at least the 3'-terminal nucleotide of the left probe are deoxyribonucleotides, wherein the target sequence is composed of ribonucleotides, (b) incubating the right probe, left probe, target sample, and T4 RNA ligase under conditions that promote hybridization of the right probe and left probe to the target sequence and that promote ligation of the right probe and the left probe, wherein the right probe and the left probe are ligated if the target sequence is present in the target sample.

2. The method of claim 1 wherein the right probe and the left probe are the 5' end and 3' end, respectively, of the same open circle probe, wherein ligation of the right probe and the left probe forms an amplification target circle.

3. The method of claim 2 wherein the method further comprises (c) bringing into contact a rolling circle replication primer and the amplification target circle, and incubating the rolling circle replication primer and the amplification target circle under conditions that promote hybridization between the amplification target circle and the rolling circle replication primer, and (d) bringing into contact DNA polymerase, the amplification target circle, and the rolling circle replication primer, and incubating the DNA polymerase, the amplification target circle, and the rolling circle replication primer under conditions that promote replication of the amplification target circle, wherein replication of the amplification target circle results in the formation of tandem sequence DNA.

4. The method of claim 3 further comprising, simultaneous with, or following, step (d), (e) bringing into contact a secondary DNA strand displacement primer and the tandem sequence DNA under conditions that promote (i) hybridization between the

I claim:

1. A method of detecting nucleic acids, the method comprising (a) bringing into contact a right probe, a left probe, a target sample, and T4 RNA ligase, tandem sequence DNA and the secondary DNA strand displacement primer, and (ii) replication of the tandem sequence DNA, wherein replication of the tandem sequence DNA results in the formation of secondary tandem sequence DNA.

5. The method of claim 3 further comprising, simultaneous with, or following, step (d),
   (e) bringing into contact RNA polymerase and the tandem sequence DNA under conditions that promote transcription of the tandem sequence DNA, wherein transcription of the tandem sequence DNA results in the formation of tandem sequence RNA.

6. The method of claim 3 wherein the rolling circle replication primer is coupled to a specific binding molecule, wherein the specific binding molecule is bound to a target molecule.

7. The method of claim 3 wherein the tandem sequence DNA is collapsed by mixing collapsing probes with the tandem sequence DNA, and incubating under conditions that promote hybridization between the collapsing probes and the tandem sequence DNA.

8. The method of claim 7 further comprising, prior to or simultaneous with the mixing of the collapsing probes with the tandem sequence DNA, mixing detection probes with the tandem sequence DNA, and incubating under conditions that promote hybridization between the detection probes and the tandem sequence DNA.

9. The method of claim 2 wherein the target sequence comprises a 5' region, a 3' region, and a central region located between the 5' region and the 3' region,
   wherein the right probe and the left probe are complementary to the 5' region and the 3' region, respectively, of the same target sequence,
   wherein neither the left probe portion of the open circle probe nor the right probe portion of the open circle probe is complementary to the central region of the target sequence, and
   wherein step (a) further comprises bringing into contact one or more gap oligonucleotides and the right probe, left probe, target sample, and T4 RNA ligase, wherein each gap oligonucleotide is complementary all or a portion of the central region of the target sequence.

10. The method of claim 1 wherein the right probe or the left probe is coupled to a substrate.

11. The method of claim 10 wherein the substrate is a surface to which other probes are coupled in an array.

12. The method of claim 10 wherein the substrate is a magnetic bead.

13. The method of claim 1 wherein the right probe, the left probe, or both are coupled to a detection label.

14. The method of claim 13 wherein either the right probe is coupled to a substrate and the left probe is coupled to a detection label, or the left probe is coupled to a substrate and the right probe is coupled to a detection label, and
   wherein ligation of the left probe to the right probe causes the detection label to become coupled to the substrate.

15. The method of claim 14 wherein the substrate is a surface to which other probes are coupled in an array or the substrate is a bead.

16. The method of claim 1 wherein the target sample is a sample of mRNA.

17. The method of claim 1 wherein the target sample is a collection of immobilized nucleic acids.

18. The method of claim 1 wherein the target sample is a nucleic acid sample obtained from cells, tissue, a bodily fluid, an environmental sample, or in vitro nucleic acid synthesis.

19. The method of claim 18 wherein the nucleic acid sample is obtained from cells.

20. The method of claim 19 wherein the cells are from a human.

21. The method of claim 1 wherein the ligated left and right probes are amplified using the ligase chain reaction.

22. The method of claim 21 wherein amplification of the ligated left and right probes is accomplished by
   (c) bringing into contact a left complement probe, a right complement probe, the ligated right and left probes, and ligase, wherein the left complement probe is complementary to the left probe and the right complement probe is complementary to the right probe,
   (d) incubating the left complement probe, right complement probe, the ligated right and left probes, and ligase under conditions that promote hybridization of the left complement probe and right complement probe to the ligated right and left probes and that promote ligation of the left complement probe and the right complement probe,
   (e) bringing into contact a left probe and a right probe, the ligated right and left complement probes, a left complement probe and a right complement probe, and the ligated right and left probes,
   (f) incubating the left probe, the right probe, the left complement probe, the right complement probe, the ligated right and left probes, the ligated left and right complement probes, and ligase under conditions that promote hybridization of the left complement probe and right complement probe to the ligated right and left probes, that promote hybridization of the left probe and right probe to the ligated right and left complement probes, that promote ligation of the left probe and the right probe, and that promote ligation of the left complement probe and the right complement probe,
   (g) repeating steps (e) and (f) one or more times.

23. The method of claim 22 wherein steps (c) and (e) and steps (d) and (f) are performed simultaneously.

24. The method of claim 1 wherein the target sequence is part of an RNA of interest, wherein the ligated right and left probes are used to prime reverse transcription of the RNA of interest to form cDNA, and wherein the cDNA is amplified using the polymerase chain reaction.

25. The method of claim 24 wherein reverse transcription and the polymerase chain reaction are accomplished by
   (c) incubating the ligated left and right probes, the RNA of interest, and reverse transcriptase under conditions that promote synthesis of a cDNA of the RNA of interest,
   (d) bringing into contact the cDNA, a right PCR primer and a left PCR primer, and a thermostable polymerase, wherein the right and left PCR primers are complementary to opposite strands of the cDNA, and wherein the right and left PCR primers flank a region of interest of the cDNA,
   (e) incubating the cDNA, the right PCR primer the left PCR primer, and the thermostable polymerase under conditions that promote cycles of primer hybridization, nucleic acid synthesis, and strand denaturation.

26. The method of claim 1 wherein the incubation of the right probe, left probe, target sample, and T4 RNA ligase is carried out in the presence of at least one additive that alters the melting temperature of hybridized nucleic acid strands.

27. The method of claim 26 wherein the additive is formamide.

28. A kit comprising a right probe, a left probe, and T4 RNA ligase,
   wherein the right probe and the left probe are designed to hybridize to a target sequence such that the 5' end of the right probe and the 3' end of the left probe are adjacent and can be ligated, wherein at least the 5'-terminal nucleotide of the right probe and at least the 3'-terminal nucleotide of the left probe are deoxyribonucleotides, wherein the target sequence is composed of ribonucleotides.

29. The kit of claim 28 wherein the right probe and the left probe are the 5' end and 3' end, respectively, of an open circle probe.

30. The kit of claim 28 wherein the right probe or the left probe is coupled to a substrate.

31. The kit of claim 30 wherein the substrate is a surface to which other probes are coupled in an array.

32. The kit of claim 30 wherein the substrate is a magnetic bead.

33. The kit of claim 28 wherein the right probe or the left probe is coupled to a detection label.

34. The kit of claim 33 wherein the detection label is a radioactive isotope, fluorescent molecule, phosphorescent molecule, enzyme, antibody, or ligand.

35. The kit of claim 28 wherein either the right probe or the left probe is coupled to a substrate and wherein the other probe is coupled to a detection label.

36. A composition comprising a right probe, a left probe, a target sample, and T4 RNA ligase, wherein the right probe and the left probe are designed to hybridize to a target sequence such that the 5' end of the right probe and the 3' end of the left probe are adjacent and can be ligated, wherein at least the 5'-terminal nucleotide of the right probe and at least the 3'-terminal nucleotide of the left probe are deoxyribonucleotides, wherein the target sequence is composed of ribonucleotides.

* * * * *